(12) United States Patent  
Pagani et al.

(10) Patent No.: US 7,279,138 B2  
(45) Date of Patent: Oct. 9, 2007

(54) HORIZONTAL CHEMICAL REACTOR, IN PARTICULAR FOR METHANOL SYNTHESIS

(75) Inventors: Giorgio Pagani, Milan (IT); Enrico Rizzi, Grandate (IT); Umberto Zardi, Breganzona (CH)

(73) Assignee: Methanol Casale S.A. (CH)

( * ) Notice: Subject to any disclaimer, the term of this patent is extended or adjusted under 35 U.S.C. 154(b) by 757 days.

(21) Appl. No.: 10/804,896

(22) Filed: Mar. 19, 2004

(65) Prior Publication Data

US 2004/0184976 A1    Sep. 23, 2004

(30) Foreign Application Priority Data

Mar. 20, 2003   (CN) .................... 03 1 07444

(51) Int. Cl.  
*B01J 8/04*   (2006.01)

(52) U.S. Cl. .......... 422/148; 422/205; 422/190; 422/193; 422/202; 423/359; 423/360; 423/361; 23/288; 208/165

(58) Field of Classification Search .......... 422/148, 422/205, 190, 193, 202; 423/359–361; 23/288; 208/165  
See application file for complete search history.

(56) References Cited

U.S. PATENT DOCUMENTS

| | | | | |
|---|---|---|---|---|
| 2,483,178 | A | * | 9/1949 | Boninger .................... 422/221 |
| 2,505,850 | A | * | 5/1950 | Briggs ........................ 422/221 |
| 4,696,799 | A | | 9/1987 | Noe |
| 4,919,909 | A | * | 4/1990 | Lesur et al. ................. 423/360 |
| 5,891,405 | A | * | 4/1999 | Bianchi et al. .............. 422/191 |

FOREIGN PATENT DOCUMENTS

| | | |
|---|---|---|
| DE | 24 49 789 A | 3/1976 |
| DE | 33 10772 A | 9/1984 |
| FR | 2 138 701 A | 1/1973 |
| FR | 2 182 009 A | 12/1973 |
| GB | 670 299 A | 4/1952 |
| WO | WO9524961 * | 9/1995 |

* cited by examiner

*Primary Examiner*—Glenn Caldarola  
*Assistant Examiner*—Vinit H Patel  
(74) *Attorney, Agent, or Firm*—Akerman Senterfitt

(57) ABSTRACT

A horizontal chemical reactor comprises at least one catalytic bed (5a-5d) arranged horizontally in the reactor and comprising a lower gas-permeable wall (6) for gas outlet, and a holding element (2) of the at least one catalytic bed.

17 Claims, 2 Drawing Sheets

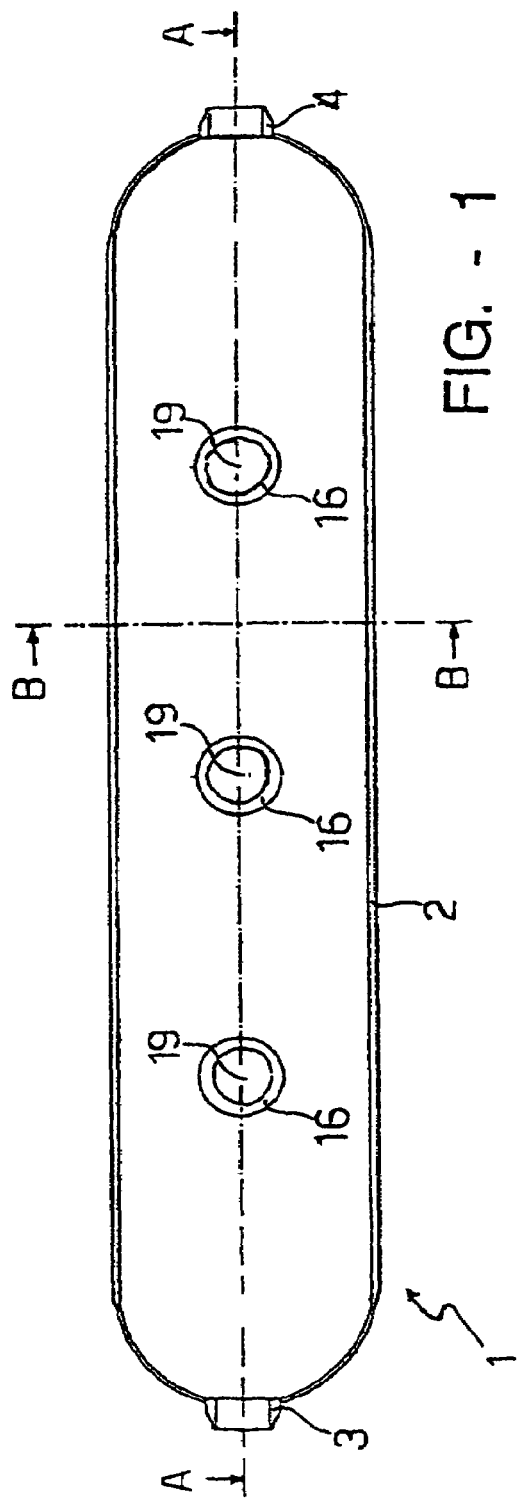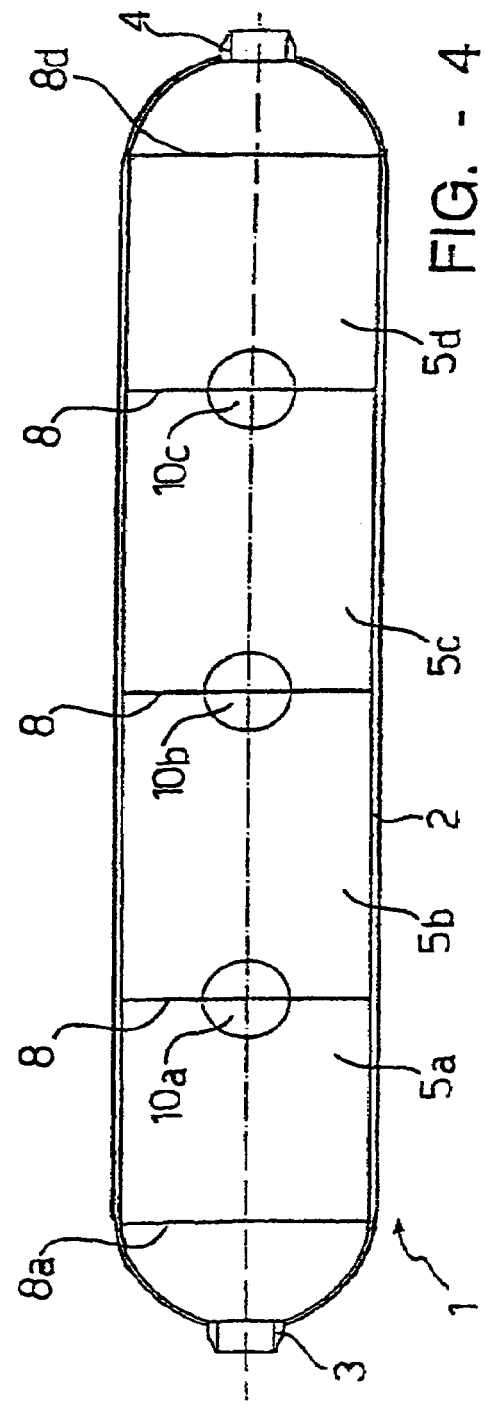

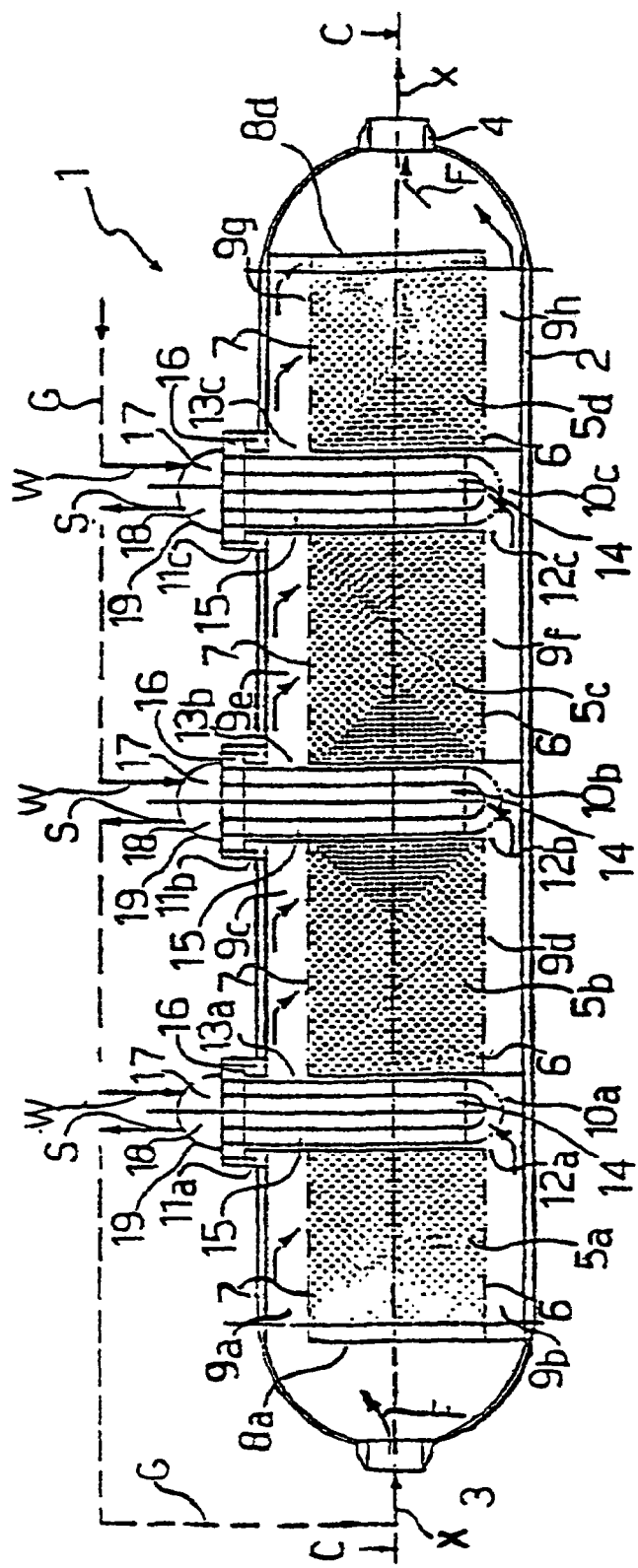
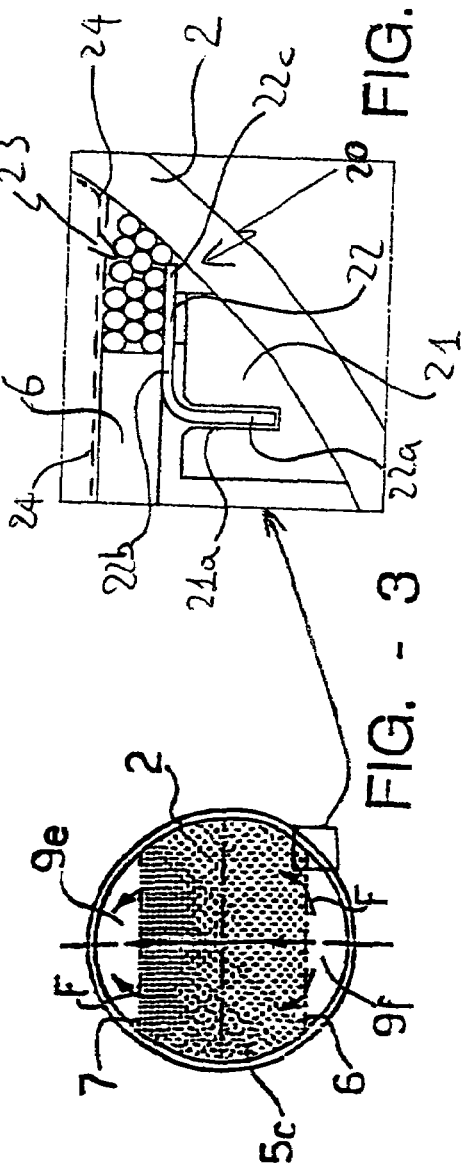
FIG. - 2
FIG. - 3
FIG. - 5

HORIZONTAL CHEMICAL REACTOR, IN PARTICULAR FOR METHANOL SYNTHESIS

FIELD OF APPLICATION

The present invention relates to a horizontal chemical reactor. More particularly, the invention concerns a reactor for heterogeneous exothermic synthesis and in particular but not exclusively for methanol synthesis.

As known, in the field of heterogeneous exothermic synthesis in general, and more in particular in the production of methanol, the requirement for synthesis reactors having high productivity and conversion yield and at the same time low energy consumption and investment cost is increasingly felt.

PRIOR ART

For this purpose there has for some time been proposed as an alternative for the conventional vertical synthesis reactors with one or more catalytic beds the adoption of reactors with greater capacity arranged horizontally.

For example, in U.S. Pat. No. 4,696,799 there is described a horizontal reactor for heterogeneous exothermic synthesis of ammonia and comprising a cartridge in which are supported a plurality of catalytic beds in mutually spaced relationship.

In the cartridge are also provided cooling means comprising in particular two gas/gas heat exchangers for indirect cooling of the partially reacted synthesis gases flowing from the first and second catalytic beds.

More advantageous in many ways, the horizontal reactor described above exhibits a series of drawbacks, the first of which is poor accessibility to all the internal parts of the reactor and in particular to the cooling means provided in the cartridge.

To perform any kind of maintenance operation on said means, e.g. replacement of defective or failed parts, it is necessary to remove the entire cartridge from the reactor, proceed with the required maintenance operations and lastly put the repaired cartridge back in the reactor.

As a consequence any work done on the reactor once it is in operation is long, difficult and especially costly.

Furthermore a reactor such as that just described comprises great structural complexity making practical construction difficult.

In this respect it is worth nothing that due to the different operating temperatures within the reactor vessel, which cause a thermal expansion of the cartridge which is different from that of the catalytic beds, it is not possible to provide a reliable and effective sealing between the cartridge and the beds, in particular the catalyst supporting bottoms of the beds. This results in an unavoidable catalyst leakage from the beds and thus in a loss of the overall reaction volume which negatively effects the reaction yield and the productivity of the reactor.

In the art, it has also been proposed a horizontal catalytic chemical reactor, wherein the reactor shell directly supports and contains the catalytic beds and the cooling means.

Although more advantageous in terms of manufacture and maintenance with respect the rector with cartridge, this kind of reactor suffers even more of the drawback related with the catalyst leakage.

In general, due the high fabrication tolerances required for manufacturing the reactor, the internal surface of the shell results to be wrinkled and its dimensions (diameter, ovalization and linearity) diverge from the design ones. Therefore, it is not possible to ensure a precise, constant and reliable connection between the shell and the catalyst support bottoms of the catalytic beds arranged within the shell.

Moreover, since the shell and the catalyst support bottoms are made of quite different materials, which are subjected to quite different operating temperatures, it results that they thermally expand in a substantial different way.

As a consequence, the conventional sealing means, such as the packing rope sealing, are not at all suitable to compensate these thermal expansions as well as to ensure an effective connection between these parts, and thus catalyst leakage from the catalytic beds occurs. Bigger is the diameter of the shell diameter higher will be such a leakage.

Because of these disadvantages, the horizontal reactors of the type considered have found rather limited use heretofore in the field of heterogeneous exothermic synthesis.

SUMMARY OF THE INVENTION

The technical problem underlying the present invention is to make available a horizontal chemical reactor, in particular for heterogeneous exothermic synthesis, having high productivity, high conversion yield, and low energy consumption and investment cost, which would be simple to construct and allow easy maintenance.

The technical problem is solved by a horizontal chemical reactor, comprising:
- at least one catalytic bed arranged horizontally in said reactor and comprising a lower gas-permeable wall for gas outlet,
- a holding element of said at least one catalytic bed, characterized in that it further comprises
- catalyst sealing means comprising a support element fixed to said holding element below said lower gas-permeable wall, a connecting element fixed at one end to said support element and supporting at an intermediate portion thereof a side end of the lower gas-permeable wall, a plurality of filling elements of predetermined size, which are arranged between the side end of the lower gas-permeable wall and an inner wall of said holding element and supported by said connecting element at a portion thereof protruding from said intermediate portion towards said inner wall of the holding element.

Further characteristics and the advantages of the chemical reactor according to the present invention are set forth in the description of an embodiment thereof given below by way of non-limiting example with reference to the annexed drawings.

BRIEF DESCRIPTION OF THE DRAWINGS

In the drawings:

FIG. 1 shows a plan view of a horizontal chemical reactor in accordance with the present invention, FIG. 2 shows a longitudinal cross section view of the horizontal reactor of FIG. 1, taken along lines A-A of FIG. 1, FIG. 3 shows a cross section view of the horizontal reactor of FIG. 1, taken along lines B-B of FIG. 1, FIG. 4 shows another longitudinal cross section of the horizontal reactor of FIG. 1, taken along lines C-C of FIG. 2, and FIG. 5 shows a detail of the cross section view of the horizontal reactor of FIG. 3.

DETAILED DESCRIPTION OF A PREFERRED EMBODIMENT

With reference to the example of FIGS. 1-5, reference number 1 indicates as a whole a horizontal chemical reactor, preferably for heterogeneous exothermic synthesis and in particular for methanol synthesis.

The reactor 1 comprises and external tubular shell 2 fitted at its ends with openings 3, 4 respectively for inlet of reagent gases and outlet of the reaction products.

5a-5d indicate a plurality of catalytic beds arranged horizontally and side by side in the shell 2, along a longitudinal axis x-x of the reactor 1, and comprising opposed gas permeable walls 6, 7 respectively lower and upper. In this example, the shell 2 constitutes the reactor holding element of the catalytic beds.

The upper gas permeable wall 7 has the function of avoiding an excessively violent impact of the gaseous reagents on the catalyst. Said wall is therefore not required in the case of a low-velocity gas flow. The gas-permeable wall 6 has the function of supporting the catalytic mass.

According to the present invention, the lower gas-permeable wall 6 is advantageously connected to the inner wall of shell 2 by sealing means 20—as shown in FIG. 5—so as to avoid undesired catalyst leakage from catalytic beds 5a and 5d.

In particular, in order to avoid that catalyst can undesirably exits the respective catalyst beds through the gaps present between the lower gas-permeable wall 6 and the inner wall-of shell 2, means 20 advantageously comprises a support element 21 fixed to the shell 2 below said lower gas-permeable wall 6, a connecting element 22 fixed at one end 22a to said support element 21 and supporting at an intermediate portion 22b thereof the side end of the lower gas-permeable wall 6.

Moreover, means 20 further comprises a plurality of filling elements 23 of predetermined size, which are arranged between the side end of the lower gas-permeable wall 6 and the inner wall of shell 2. Filling elements 23 are advantageously supported by said connecting element 22 at a portion 22c thereof, protruding from said intermediate portion 22b towards the inner wall of the shell.

Means 20 ensures—in a simple and economic way—an effective, reliable and durable catalyst sealing, between the lower gas-permeable wall 6 and the shell 2, which is easy to manufacture and does not require particular maintenance. It follows that, thank to the present invention, losses of catalyst mass are practically totally avoided to all advantage of an optimal operation of the catalytic reactor as well as to the ensuing reaction yield and productivity of the reactor.

Preferably, the connecting element 22 is "L shaped" and is fixed in a removable manner to the support element 21. Preferably, end 22a of support element 22 is simply inserted in an aperture 21a of support element 21.

Furthermore, the filling elements 23 preferably comprise inert balls, such as ceramic balls, or metallic balls. Advantageously, the filling elements 23 are thus made of hard material, not subjected to wear or erosion, maintaining their sealing properties constant with the time.

The filling elements 23 have a size (diameter) that is substantially bigger than the diameter of the catalyst contained in the catalytic beds, in any case bigger than the remaining gap between the end portion 22c of connecting element 22 and the inner wall of the shell 2, taking into account all possible thermal expansions of these parts.

According to a preferred embodiment of the sealing means 20 of the present invention, the filling elements 23, and preferably also at least part of the lower gas-permeable wall 6, are covered by a suitable wire mesh, so as to avoid that the catalyst penetrate within the filling elements 23, with the risk of being damaged. In the example of FIG. 5, the wire mesh is indicated by broken line 24 and advantageously also extends over the inner wall of the shell 2.

Advantageously, the sealing means 20 of the present invention is also applicable in chemical reactors, wherein the catalytic bed holding element is a cartridge (not shown) arranged within the shell.

Preferably, the beds 5a-5d are adjacent and mutually separated by a plurality of baffles, all indicated by 8, extending transversally to the longitudinal axis x-x of the reactor 1. 8a and 8d indicate opposed closing side walls of the catalytic beds 5a and 5d respectively. A plurality of air spaces 9a-9h are defined between the inner wall of the shell 2 and the gas-permeable walls 6 and 7 of the beds 5a-5d for passage of the gases from one catalytic bed to the other.

Between the catalytic beds 5a-5d is defined a plurality of cylindrical chambers 10a, 10b, 10c extending transversally to the beds and accessible from the outside of the shell 2 through respective apertures 11a, 11b, 11c.

Each of said chambers 10a, 10b, 10c is equipped with opposed passages 12a, 13a to 12c, 13c for inlet and outlet of gas respectively, which open in correspondence of the air spaces 9a-9h. A plurality of fluid paths is defined in this manner between pairs of adjacent beds 5a-5d.

In FIG. 2 inside the chambers 10 are housed in a removable manner respective cooling means 14 for the indirect cooling of the gases flowing between said adjacent beds 5a-5d. Advantageously, the cylindrical shaped chamber 10 in which are housed the cooling means, are particularly suitable for optimal heat exchange between the partially reacted hot gases and the cooling fluid.

Said cooling means 14 comprise a plurality of U-shaped tubes 15 extending into the chambers 10a-10c. The ends of the tubes 15 are in fluid communication through a tube plate 16 with respective chambers 17, 18 for inlet and outlet of cooling fluid.

The chambers 17, 18 are made in a cover 19 of the cooling means 14, which is integral with the tube plate 16.

The tube plate 16 is fixed in a conventional removable manner to the shell 2 in correspondence of the apertures 11a-11c, e.g. by bolting.

In a preferred embodiment said cooling means 14 use water as cooling fluid and therefore constitute essentially a boiler for high thermal level steam generation. There is thus achieved advantageously a recovery at high thermal level of the reaction heat to generate the high pressure steam usable in other parts of the plant.

As an alternative the means 14 can use as cooling fluid a part of the cold reagent gases, thus constituting a preheater for the reagent gases.

In another embodiment (not shown) the boiler or heat exchanger can be of the bayonet type.

The flow of cooling fluid through said cooling means 14 can be of the natural circulation type or of the forced circulation type.

Thanks to the special structure of the horizontal reactor, it is now possible to accede easily to the cooling means, which can be easily replaced independently while avoiding all risk of damage to the other reactor parts. In this manner the maintenance and repair operations on the cooling means are technically simple and economical.

Moreover, the arrangement of the removable cooling means in special chambers 10 arranged between the catalytic beds and accessible from outside the shell also permits to carry out simply and effectively the maintenance of the catalytic bed, with particular reference to the loading and unloading of the catalyst.

Indeed, thanks to the presence of the above said chambers it is now possible to reduce the number of manholes and handholes necessary for such loading and unloading operations as compared with the known horizontal reactors.

Another advantage of this horizontal reactor lies in its flexibility of use both as concerns the possibility of using interchangeably in the same reactor cooling means of different kinds, e.g. to produce high thermal level steam or for preheating the gaseous reagents supplied in the reactor, but also as concerns the possibility to vary the internal configuration of the reactor by housing the cooling means in the chambers in the desired sequence to perform or not indirect cooling between one bed and the other depending on the synthesis reaction it is intended to carry out.

In the latter case the shell is advantageously provided with removable covers arranged in correspondence of the chambers not occupied by cooling means.

In FIGS. 2 and 3 the arrows F indicate the various paths taken by the gaseous reagents along the air spaces 9a-9h through the catalytic beds 5a-5d and the cooling means 14.

In FIG. 2 the arrows W and S indicate respective paths for the cooling water entering the chambers 17 and the steam leaving the chambers 18.

The broken-line arrows G indicate the path of the cold synthesis gas preheated by the means 14 in the preheater version.

Operation of the horizontal reactor of the present invention is as follows.

With reference to FIG. 2 a flow of reagent gases, e.g. $H_2$, CO and $CO_2$ already preheated to reaction temperature (approximately 240° C.) is let into the reactor 1 through the opening 3 for gas inlet, flows along the air space 9a and traverses adiabatically the first catalytic bed 5a from the top downward.

The partially reacted gases come out of the latter at a temperature of approximately 290° C. and enter through the passage 12a into the chamber 10a where they are cooled by indirect thermal exchange with a flow of water passing through the tubes 15 of the boiler 14.

In this manner the synthesis gas is brought to the initial temperature with simultaneous high pressure steam generation, e.g. 20-25 bar. The steam thus produced can be advantageously used, e.g. in the methanol distillation phase.

The cooled flow of partially reacted gas leaving the chamber 10a is collected in the air space 9c an then enters the second bed 5b in a manner analogous to that described above.

The reaction products coming from the last bed 5d come out of the reactor through the opening 4.

The horizontal reactor thus conceived has optimal thermodynamic efficiency comparable in the methanol synthesis field to that of an isotherm reactor of equal catalytic volume, which is known to allow achievement of the highest conversion yield.

Advantageously the horizontal bed according to the present invention having a very simple internal structure and of modular type can contain a variable number of catalytic beds, preferably at least two intercalated with cooling means, compatibly with the internal pressure conditions in the shell.

Particularly satisfactorily results have been obtained with four adiabatic catalytic beds with three intermediate cooling means (as in the example shown), or three adiabatic catalytic beds and two intermediate cooling means.

In addition, thanks to the presence of catalytic beds arranged side by side and at least partly adjacent, it is possible to achieve a high degree of utilization of the useful volume of the reactor, which can be occupied even up to 80-83% by the catalyst.

Consequently, for equal installed catalyst volume the reactor according to the present invention will have a smaller pressure body (shell) than that of a reactor of the prior art, with considerable material economy.

It will be appreciated that the horizontal reactor in accordance with the present invention is advantageously applicable for heterogeneous exothermic synthesis of different types compatibly with the reactor structure.

The invention thus conceived is susceptible to further embodiments and modifications all falling within the skill of the man skilled in the art and, as such, falling within the scope of protection of the invention itself, as it is defined by the following claims.

The invention claimed is:

1. Horizontal chemical reactor, comprising:
   at least one catalytic bed (5a-5d) arranged horizontally in said reactor and comprising a lower gas-permeable wall (6) for gas outlet,
   a holding element (2) of said at least one catalytic bed (5a-5d),
   characterized in that it further comprises
   catalyst sealing means (20) comprising a support element (21) fixed to said holding element (2) below said lower gas-permeable wall (6), a connecting element (22) fixed at one end (22a) to said support element (21) and supporting at an intermediate portion (22b) thereof a side end of the lower gas-permeable wall (6), a plurality of filling elements (23) of predetermined size, which are arranged between the side end of the lower gas-permeable wall (6) and an inner wall of said holding element (2) and supported by said connecting element (22) at a portion (22c) thereof protruding from said intermediate portion (22b) towards said inner wall of the holding element (2).

2. Reactor according to claim 1, characterized in that the connecting element (22) is L-shaped.

3. Reactor according to claim 1, characterized in that the connecting element (22) is fixed in a removable manner to the support element (21).

4. Reactor according to claim 3, characterized in that the said one end (22a) of the connecting element (22) is inserted in an aperture (21a) of the support element (21).

5. Reactor according to claim 1, characterized in that the filling elements (23) comprise inert balls.

6. Reactor according to claim 1, characterized in that the filling elements (23) are covered by a wire mesh (24).

7. Reactor according to claim 1, wherein the holding element (2) is a cartridge arranged within the reactor.

8. Reactor according to claim 1, characterized in that the holding element is an external shell (2) of the reactor of substantially cylindrical shape, and in that it comprises:
   at least two catalytic beds (5a-5d) arranged horizontally and side by side in said shell (2) and comprising said lower gas-permeable wall (6) for gas outlet,
   at least one chamber (10a-10c) extending between said at least two catalytic beds (5a-5d) and accessible from the outside of the shell (2),
   a fluid path for the gases flowing between said beds (5a-5d) defined in said at least one chamber (10a-10c) between opposed passages (12a,13a-12c,13c) for gas inlet and outlet, and
   cooling means (14) housed in a removable manner in said at least one chamber (10a-10c) for indirect cooling of the gases flowing between said beds (5a-5d).

9. Reactor according to claim 8 characterized in that said at least two catalytic beds (5a-5d) are adjacent.

10. Reactor according to claim 8, further comprising a plurality of air spaces (9a-9h) for passage of the gases from and to said beds (5a-5d) defined between the internal wall of the shell (2) and opposed upper and lower surfaces (7,6) of said beds.

11. Reactor according to claim 10 characterized in that said passages (12a,13a-12c,13c) for gas inlet to and outlet from said at least one chamber (10a-10c) are open in correspondence of said air spaces (9a-9h).

12. Reactor according to claim 8 characterized in that said at least one chamber (10a-10c) is substantially cylindrical in shape.

13. Reactor according to claim 8 characterized in that said cooling means comprise at least one boiler (14) for high thermal level steam generation.

14. Reactor according to claim 8 characterized in that said boiler (14) is of the tube nest or bayonet type.

15. Reactor according to claim 14 characterized in that said boiler (14) is of the natural or forced circulation type.

16. Reactor according to claim 8 characterized in that said cooling means comprise at least one gas/gas heat exchanger (14).

17. Reactor according to claim 5, wherein the inert balls are ceramic balls or metallic balls.

* * * * *